(12) United States Patent
Callahan et al.

(10) Patent No.: US 9,104,903 B2
(45) Date of Patent: Aug. 11, 2015

(54) MICROSCOPY VISUALIZATION

(71) Applicant: University of Utah Research Foundation, Salt Lake City, UT (US)

(72) Inventors: Steven P. Callahan, Centerville, UT (US); Bryan W. Jones, Salt Lake City, UT (US); Greg M. Jones, Cottonwood Heights, UT (US); Erik Jorgensen, Salt Lake City, UT (US); John Schreiner, Salt Lake City, UT (US); Tolga Tasdizen, Salt Lake City, UT (US); Shigeki Watanabe, Salt Lake City, UT (US); Stan Kanarowski, Salt Lake City, UT (US); Josh Cates, Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 111 days.

(21) Appl. No.: 13/846,737

(22) Filed: Mar. 18, 2013

(65) Prior Publication Data

US 2014/0126801 A1 May 8, 2014

Related U.S. Application Data

(60) Provisional application No. 61/685,392, filed on Mar. 16, 2012.

(51) Int. Cl.
| | |
|---|---|
| *G06K 9/00* | (2006.01) |
| *H01J 37/22* | (2006.01) |
| *G01N 21/64* | (2006.01) |
| *G01N 23/225* | (2006.01) |
| *G02B 21/36* | (2006.01) |

(52) U.S. Cl.
CPC .......... *G06K 9/0014* (2013.01); *G01N 21/6458* (2013.01); *G01N 23/2251* (2013.01); *G02B 21/365* (2013.01); *G06K 9/00134* (2013.01); *H01J 37/222* (2013.01); *G01N 21/648* (2013.01); *G01N 2223/071* (2013.01); *G01N 2223/612* (2013.01)

(58) Field of Classification Search
USPC .................................................. 382/128–134
See application file for complete search history.

(56) References Cited

U.S. PATENT DOCUMENTS

| | | | | |
|---|---|---|---|---|
| 4,873,440 | A * | 10/1989 | Mori et al. | 382/128 |
| 7,929,738 | B2 * | 4/2011 | Shirota et al. | 382/128 |
| 2004/0114788 | A1 * | 6/2004 | Nakazawa et al. | 382/128 |
| 2005/0267690 | A1 * | 12/2005 | Cong et al. | 702/19 |

OTHER PUBLICATIONS

Watanabe et al.; Protein localization in electron micrographs using fluorescence nanoscopy (with supplemental Notes); Nature Methods; Jan. 2011; 22 pages; vol. 8, No. 1; Nature America, Inc.

* cited by examiner

*Primary Examiner* — Alex Liew
(74) *Attorney, Agent, or Firm* — Thorpe North & Western

(57) ABSTRACT

A method is described for correlating microscopy images from a number of modalities in a sub diffraction resolution environment. The method may include receiving a number of datasets that may represent microscopy captures from a number of different modalities. The microscopy captures may contain feature markers that may be used to register a number of data points contained in a dataset with data points from another dataset. Upon registering the data points of the datasets, a combined dataset may be produced and a visual image of the combined dataset may be provided.

4 Claims, 7 Drawing Sheets

MICROSCOPY VISUALIZATION

BACKGROUND

A barrier to increasing human understanding of cellular biology may be that current techniques do not permit the visualization of proteins and cell structures in a way that allows a viewer to understand the operation of proteins in a cell. For example, technology such as fluorescence light microscopy may be widely used for protein localization with a cell, but subcellular context, such as organelles are often absent in images produced by fluorescence light microscopy. On the other hand, electron microscopy can map membranes of a cell, which in turn makes organelles inside the cell visible, but electron microscopy is limited in the ability to specifically localize proteins.

Correlative approaches may allow imaging a specimen with fluorescence light microscopy or electron microscopy, but may lack an effective process to correlate the fluorescence light microscopy image with the electron microscopy image. The low resolution of fluorescence images often precludes the precise localization of proteins in relation to specific organelles or microenvironments within a cell. Advances in sub diffraction resolution fluorescence light microscopy techniques, such as fluorescence photoactivation localization microscopy (FPALM), photoactivated localization microscopy (PALM) and direct stochastic optical reconstruction (dSTORM) may resolve protein distributions more than ten times better than conventional light microscopy. These advances in sub diffraction resolution fluorescence light microscopy have triggered the development of new correlative approaches such as nano resolution fluorescence electron microscopy (Nano-fEM). Nano-fEM localizes proteins at the nanoscale by imaging a cell sample using sub diffraction resolution localization microscopy (FPALM/dSTORM) and electron microscopy, and the datasets produced by Nano-fEM may be manually correlated to provide a visualization of protein distribution within a cell.

DETAILED DESCRIPTION

The technology relates to a method for correlating a sub diffraction resolution microscopy image with an electron microscopy image. A barrier to increasing understanding of cellular biology in research may be a gap in microscopy technology. For example, some microscopy techniques may permit proteins to be imaged, and other microscopy techniques permit cell structure to be viewed. But these microscopy techniques do not permit proteins and cell structure to be visualized together in a single image. This technology may be used to bridge the gap by enabling viewing of proteins simultaneously with cell structure in a single image.

The technology may perform a method that correlates two or more datasets representing images produced by two or more modalities (e.g., imaging modalities such as an electron microscopy, sub diffraction resolution microscopy, etc.). The method may perform an automated correlation by registering data points of the two or more datasets based upon feature markers. Feature markers may be natural features of a specimen and/or introduced elements strategically placed on or around a specimen. For instance, feature markers may include landmark markers, such as the structures of a cell (e.g., organelles, cell walls, etc.), or introduced fiducial markers such as gold or silver nanoparticles placed in or around a cell. Once registered, a combined dataset may be produced that may be used to provide a visual image of the combined datasets. Thus, by aligning and merging datasets of the representative images from the different modalities, a single image may be produced enabling both cellular structures and proteins to be visualized, resulting in a tool that may allow an enhanced understanding of cell function and may improve diagnosis and treatment of neurodegenerative diseases.

The term capture as used in this specification may refer to capturing of a dataset or a number of data points produced by a modality, such as a microscope. A captured data set may be separately converted to an image.

Figure 1:
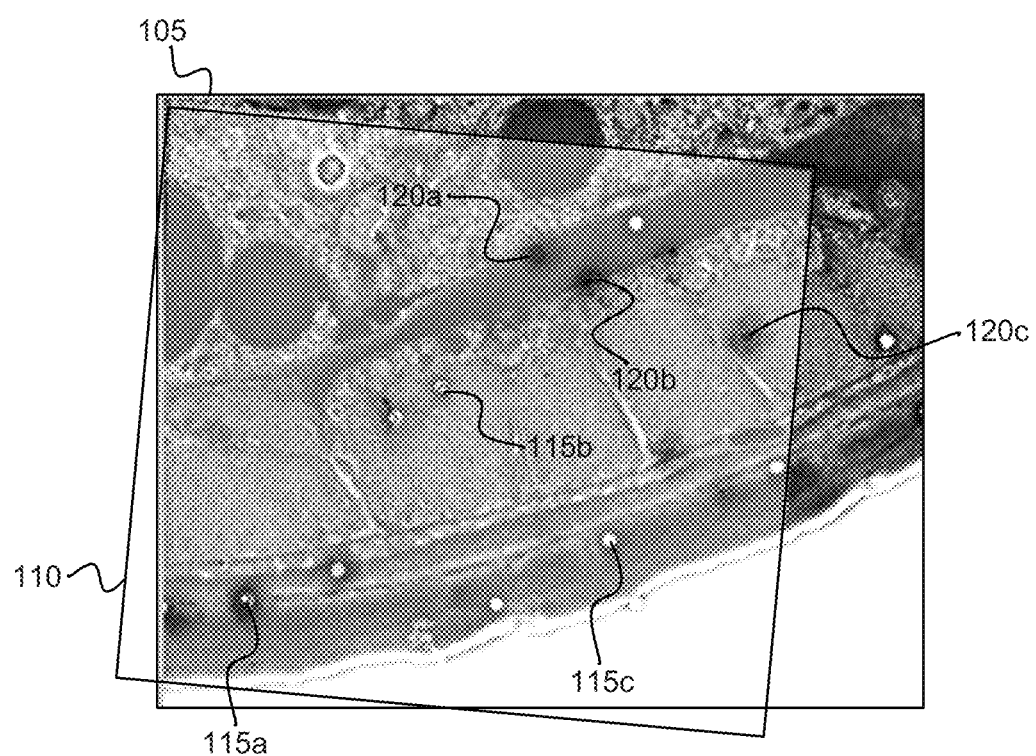
FIG. 1 is an illustration that depicts an example of a method to correlate a fluorescence microscopy image with an electron microscopy image in a sub diffraction resolution environment.

FIG. 1 is a visual illustration of an example that may correlate a sub diffraction resolution microscopy capture 110 with an electron microscopy capture 105. Sub diffraction resolution microscopy captures 110 may be one example of a modality that may be correlated with another modality, such as an electron microscopy capture 105. Sub diffraction microscopy may be an imaging technique capable of capturing a specimen using a resolution that is less than half the wavelength of light and electron microscopy may be an imaging technique that may produce a magnified image of a specimen by illuminating the specimen with an electron beam. Sub diffraction resolution microscopy captures 110 may be used, in one example, to image proteins 120a-c within a cell by tagging proteins 120a-c with fluorescence dyes. The cell may then be captured using a sub diffraction resolution microscope. In addition, the cell may be captured again using an electron microscope. The imaging process of the sub diffraction resolution microscope may produce a first dataset and the imaging process of the electron microscope may produce a second dataset. The first and the second dataset may be registered using a method that may correlate feature markers 115a-c that may be contained in both the sub diffraction resolution microscopy capture 110 and the electron microscopy capture 105. The method may identify and label the corresponding feature markers 115a-c in both datasets and map a set of data points in the first dataset to the same data points in the second dataset. Once registered, a resulting single image of the correlated sub diffraction resolution microscopy capture 110 and the electron microscopy capture 105 may be provided or rendered that shows both cellular structures and the location of proteins 120a-c within those cellular structures.

Figure 2:
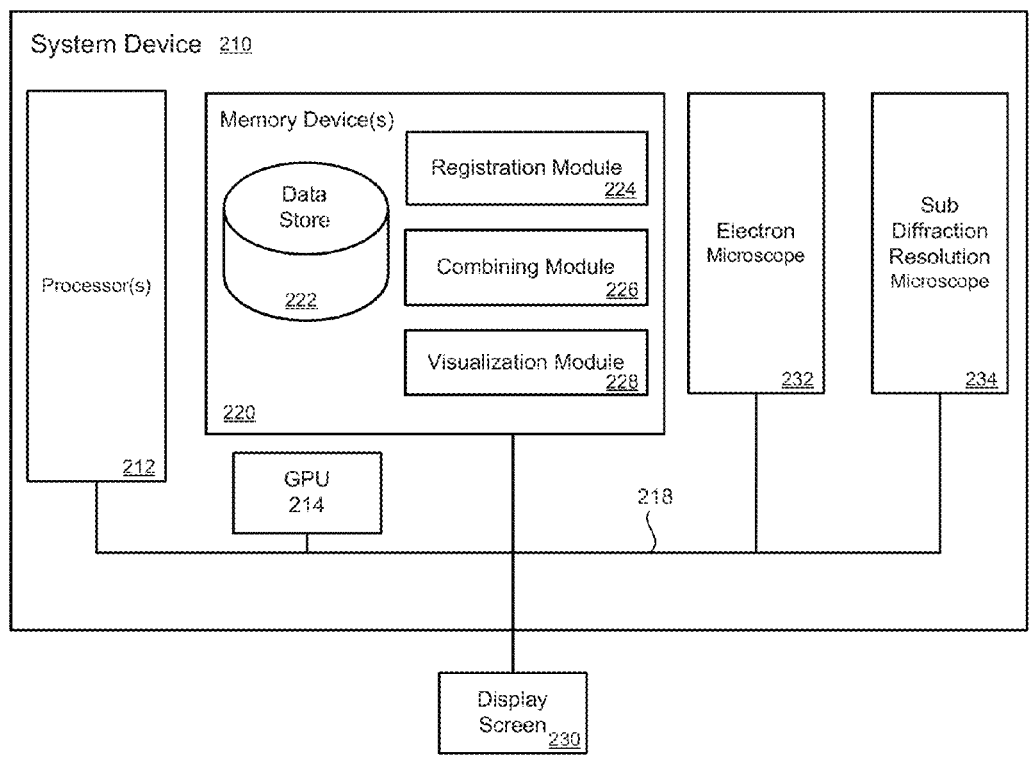
FIG. 2 is a block diagram illustration of an example of a system device to correlate microscopy images from a plurality of modalities.

FIG. 2 illustrates a high level example of a system 210 that may be used to correlate microscopy captures from a number of different modalities. The system 210 may include one or more modules located in a memory device 220 that are executable by one or more processor(s) 212. The modules may include, for example, a registration module 224, a combining module 226, a visualization module 228 and other modules that may be located in the memory device 220.

The registration module 224 may be configured to correlate two or more datasets that may be received from a number of different modalities. For example, the system 210 may include modalities such as an electron microscope 232 and a sub diffraction resolution microscope 234. The electron microscope 232 and the sub diffraction resolution microscope 234 may provide to the registration module 224 datasets that may contain feature markers. Feature markers may be landmark markers, such as a natural structure or characteristic of a cell. For example, a landmark marker may be a part of an organelle within a cell or a boundary of a cell wall. Also, feature markers may be fiduciary markers, such as gold nanoparticles, silver nanoparticles, silica beads or other introduced elements placed in a cell. These fiduciary markers may be placed in a cell and a capture of the cell may be produced using two different modalities.

Alternatively, fiducial markers such as gold or silver nanoparticles may be organized on or applied onto a microscope slide so that the fiducial markers form a visual structure that may be visible in the capture produced by a modality. Captures produced by other modalities using the same fiducial marker structure and placement on a microscope slide may be registered to the first capture using the fiducial markers.

In an alternative example, a feature marker may be metadata associated with a capture produced by a modality (e.g., an electron microscope 232 or a sub diffraction resolution microscope 234). The metadata may be used by the registration module 224 to register the captures received from the modalities. For example, metadata that may describe a capture of subject matter captured with one modality may be compared to meta data of a capture of the same subject matter captured using a different modality. Similarities in the metadata may be used to register the two captures. For example, one metadata descriptor that may be used to correlate one modality with another modality may be the field-of-view descriptor. The field-of-view descriptor may provide the size of a dataset in physical dimensions. Comparing the field-of-view metadata descriptor of two or more modality datasets may allow the datasets to be scaled to the same space. Another example of a metadata descriptor may be the position descriptor. The position descriptor may provide the position of a modality capture in relation to the microscope slide used to image a specimen or some other specified origin. The position descriptor may allow for the rough placement of one modality capture on top of another modality capture. An additional example of a metadata descriptor may be a laser and/or biomarker descriptor. For instance, depending on how a specimen may be tagged, multi-color light microscopy may be used to locate landmarks for registration in one or more specimens. The captures may then be registered based upon the matching landmarks present in the captures.

One modality that may be used to capture subject matter may be an electron microscope 232. An electron microscope 232 may include, for example, a scanning electron microscope (SEM), a type of electron microscope that produces images of a specimen by scanning the specimen with a focused beam of electrons and/or an electron tomography microscopy (tomography EM), which is a tomography technique for obtaining detailed three dimensional structures of a specimen. Because the context provided by organelle boundaries and other ultra-structural features of cells may be absent in optical images (e.g., sub diffraction resolution microscopy) due to an inadequacy of highly specific dyes with apt photophysical properties, cell structures may be best visualized using an electron microscope 232. Electron microscopes 232 may have the ability to provide resolutions of less than 1 nm and use optimized staining techniques. Although electron microscopes 232 may provide visualization of cell structures, obtaining a complete picture of protein distribution using an electron microscope 232 may be problematic. This may be because although some techniques using electron microscopes 232 can localize proteins in electron micrographs, these techniques may be limited by a lack of compatible antibodies, poor preservation of morphology and a lack of sensitivity.

For the reasons stated above, another modality may be used in combination with an electron microscope 232 to provide an image by using another technique that may, for example, localize proteins in a cell. One of these modalities may be a sub diffraction resolution microscope 234. Sub diffraction resolution microscopy may include several techniques, including for example, internal reflection fluorescence (TIRF) microscopy, single molecule localization (SML), structured illumination microscopy (SIM), multifocal structured illumination microscopy, confocal microscopy, stimulated emission depletion (STED) microscopy, wide field microscopy and atomic force microscopy (AFM). The functions of proteins may be closely associated with their location in a cell, and thus the measured distribution of a protein can often enable the elucidation of the protein's biochemical role. Similarly, aberrant trafficking of proteins is known to underlie many diseases, including some forms of cancer and neurodegenerative disorders. As such, a sub diffraction resolution microscope 234 may be used in a technique involving fluorescence microscopy to assess protein localization. Fluorescence microscopy may provide a broad palette of colors (either via organic dyes or genetically encoded reporter proteins) that may be used in imaging proteins and thus, may allow multiple proteins to be imaged in the same cell simultaneously. Until recently, fluorescent protein localization was still relatively imprecise due to the limits of optical diffraction, which may prevent accurate measurements below 250 nm. As a result, methods known as sub diffraction resolution microscopy have been developed to localize proteins to an accuracy of around 10 nm, about the size of a protein itself.

A modality (e.g., an electron microscope 232 or a sub diffraction resolution microscope 234) may provide to the registration module 224 with a dataset for a capture produced by the modality. Within the dataset may be feature markers that may be used to correlate one dataset with another dataset. For example, in some cases, a first dataset and a second dataset may contain fiducial markers (e.g., gold nanoparticles) that can be imaged across multiple modalities. In such cases, the registration module may register the datasets by labeling the corresponding fiducial markers in both datasets and solving a linear system to determine the affine transformation that maps the set of points in the first dataset to the same points in the second dataset. The registration module 224 may find the feature markers in each dataset and find the correspondence between these feature markers in the datasets.

The combining module 226 may be configured to produce a combined dataset based upon the registration of the two or more datasets. For example, once two or more datasets may have been registered and the data points contained within the datasets correlated, the datasets may be transformed into one combined coordinate system. The combined dataset may be likened to overlaying a number of images obtained from a number of modalities so that the images align with one another.

A visual image may be produced from the combined dataset by the visualization module 228. In one example, the visualization module 228 may provide a combined dataset that may be used by existing visualization software packages. For example, the combined dataset may be formatted and given a file extension for a commercially available software product. In another example, the combined dataset may be formatted for use with proprietary visualization software. Upon formatting the combined dataset by the visualization module 228, an image may be provided that displays two or more modality images overlaying one another. For example, an image may display protein localization obtained by sub diffraction resolution microscopy and cell morphology obtained by electron microscopy within the single image, thus providing an image where protein sub-cellular interactions may be seen.

In addition to providing two dimensional images, the visualization module 228 may provide a three dimensional image. For example, three dimensional datasets may be provided to the registration module 224 which may correlate the datasets based upon feature markers. The combing module 226 may combine the three dimensional datasets based on the registration of the three dimensional datasets and the visualization module 228 may then format the three dimensional datasets providing a three dimensional image. The system device 210 may include a GPU 214 (graphics processing unit) that may be used to accelerate the building of the two and/or three dimensional images in a frame buffer for output to a display 230.

A data store 222 may also be located in the memory device 220 for storing data related to the modules and other applications along with an operating system that is executable by the processor(s) 212. The term "data store" may refer to any device or combination of devices capable of storing, accessing, organizing and/or retrieving data, which may include any combination and number of data servers, relational databases, object oriented databases, flat files and data storage configurations. The storage system components of the data store 222 may include storage systems such as a SAN (Storage Area Network), volatile or non-volatile RAM, optical media, or hard-drive type media. The data store 222 may be representative of a plurality of data stores 222 as can be appreciated.

The system 210 may include one or more processors 212 that are in communication with memory devices 220. The system 210 may include a local communication interface 218 for the components in the system 210. For example, the local communication interface may be a local data bus and/or any related address or control busses as may be desired.

Other applications may also be stored in the memory device 220 and may be executable by the processor(s) 212. Components or modules discussed in this description that may be implemented in the form of software using high programming level languages that are compiled, interpreted or executed using a hybrid of the methods.

The system device may also have access to I/O (input/output) devices that are usable by the system device. An example of an I/O device is a display screen 230 that is available to display output from the system device. Other known I/O device may be used with the system device as desired. Networking devices and similar communication devices may be included in the system device that may include wired or wireless networking devices that connect to the internet, a LAN, WAN, or other computing network.

The components or modules that are shown as being stored in the memory device 220 may be executed by the processor(s) 212. The term "executable" may mean a program file that is in a form that may be executed by a processor 212. For example, a program in a higher level language may be compiled into machine code in a format that may be loaded into a random access portion of the memory device 220 and executed by the processor 212, or source code may be loaded by another executable program and interpreted to generate instructions in a random access portion of the memory to be executed by a processor. The executable program may be stored in any portion or component of the memory device 220. For example, the memory device 220 may be random access memory (RAM), read only memory (ROM), flash memory, a solid state drive, memory card, a hard drive, optical disk, floppy disk, magnetic tape, or any other memory components.

The processor 212 may represent multiple processors and the memory device 220 may represent multiple memory units that operate in parallel to the processing circuits. This may provide parallel processing channels for the processes and data in the system. The local communication interface 218 may be used as a network to facilitate communication between any of the multiple processors and multiple memories. The local communication interface 218 may use additional systems designed for coordinating communication such as load balancing, bulk data transfer and similar systems.

FIG. 2 illustrates that certain processing modules may be discussed in connection with this technology and these processing modules may be implemented as computing services. In one example configuration, a module may be considered a service with one or more processes executing on a server or other computer hardware. Such services may be centrally hosted functionality or a service application that may receive requests and provide output to other services or consumer devices. For example, modules providing services may be considered on-demand computing that are hosted in a server, cloud, grid or cluster computing system. An application program interface (API) may be provided for each module to enable a second module to send requests to and receive output from the first module. Such APIs may also allow third parties to interface with the module and make requests and receive output from the modules. While FIG. 2 illustrates an example of a system 210 that may implement the techniques above, many other similar or different environments are possible. The example environment discussed and illustrated above are merely representative and not limiting.

Figure 3:
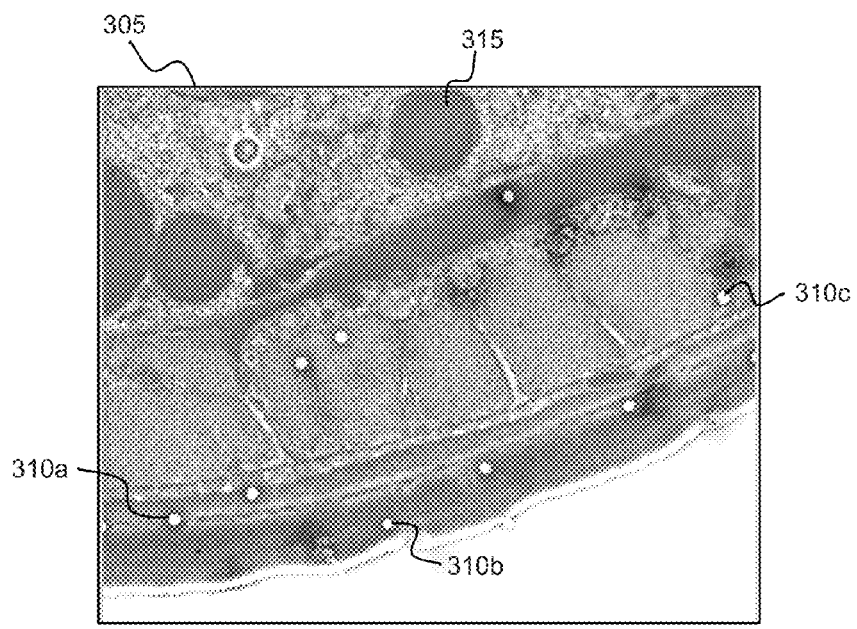
FIG. 3 is an illustration that depicts an example of an electron microscopy image.

FIG. 3 illustrates an example of an electron microscopy image 305 of a cell containing a number of feature markers 310*a-c* and 315. An electron microscope may be one modality used by the technology that may produce a magnified image of a specimen by illuminating the specimen with an electron beam. An electron microscope may be used to image specimens such as microorganisms, cells, large molecules, metals, crystals, etc. and may provide resolutions of less than one nanometer. An electron microscope may have the ability to map cell membranes, and therefore cell organelles. The electron microscope may be limited in the ability to specifically localize proteins within a cell due to a lack of suitable labeling of the proteins. Immunocytochemical electron microscopy (immuno-EM) may be used to localize proteins to organelles. However, this method may be compromised by technical difficulties including the destruction of antigens, inaccessibility of antigens, the lack of suitable antibodies and nonspecific binding of antibodies. When the method is used successfully, the size of antibodies (~19 nm long) may limit the ultimate resolution, particularly when secondary antibodies may be used.

The cell represented in the electron microscopy image 305 shows natural landmarks contained within the cell that may be used as a feature marker 315 as well as introduced fiducial markers 310a-c. Feature markers 315 may be, for example, landmarks such as cell walls, organelles within a cell or other natural characteristics of a cell. Fiducial markers 310a-b may be introduced elements placed within a cell or on a microscope slide. Feature markers may be used to register one image from a modality with another image from a different modality. For example, the electron microscopy image 305 may be registered with an image obtained from another modality based upon the feature markers 310a-c and 315 contained within the electron microscopy image 305.

Figure 4:
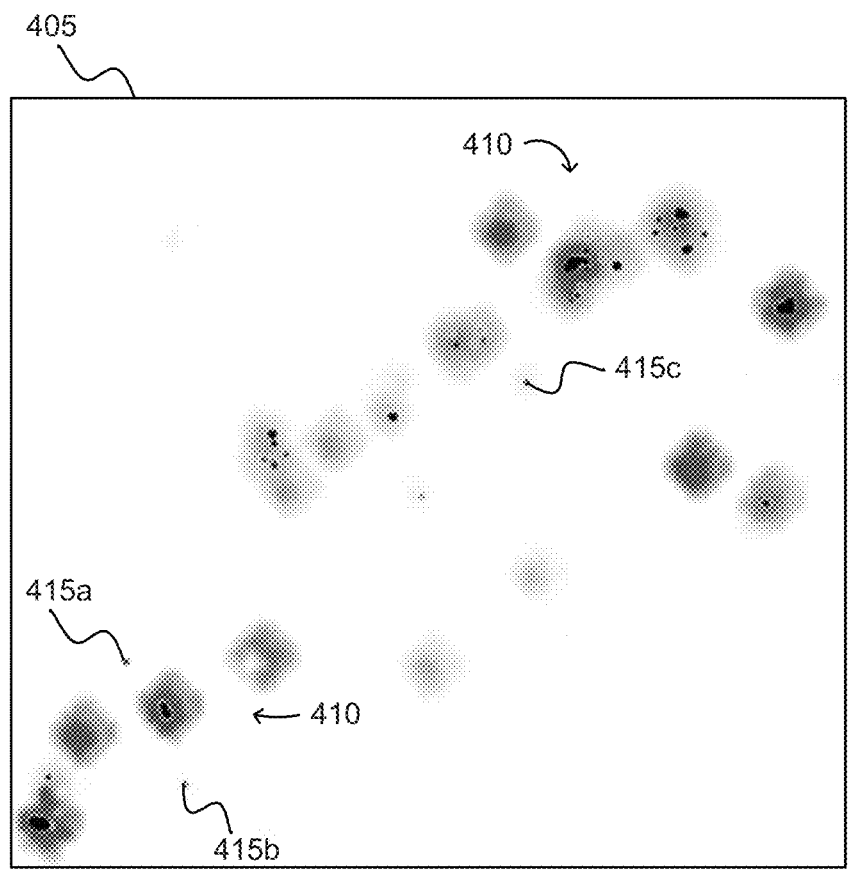
FIG. 4 is an illustration that depicts an example of a sub diffraction resolution microscopy image.

FIG. 4 illustrates another example of an image that may be provided by a modality. The sub diffraction resolution microscopy image 405 shows a number of proteins 410 contained within a cell. The sub diffraction resolution image also contains a number of feature markers that may include fiducial markers 415a-b, which may be introduced elements placed within the cell.

Sub diffraction resolution microscopy may be a form of light microscopy that may include fluorescence techniques capable of nanometer-scale resolution (nanoscopy), which permit separation of fluorophores closer than the diffraction limit. Sub diffraction resolution microscopy may involve using stimulated emission depletion (STED) microscopy where fluorescence may be inhibited by a beam of light, called the STED beam. Patterned as a doughnut and overlaid with the excitation beam of a scanning microscope, the STED beam may ensure that fluorophores in a narrow region around the doughnut center are allowed to fluoresce and the other molecules illuminated by the excitation light remain dark.

The techniques of sub diffraction resolution microscopy may include direct stochastic optical reconstruction (dSTORM), photoactivated localization microscopy (PALM), fluorescence photoactivated localization microscopy (FPALM) or stochastic optical reconstruction microscopy (STORM). These techniques use molecules whose fluorescence can switch (blink) and may be activated or deactivated by the absorption of a photon with or without the presence of chemical components. The technique may separate features that may be closer than a diffraction limit by randomly activating one fluorophore and leaving neighboring molecules dark. The position of the fluorophore may be determined by calculating the centroid of an emission pattern. The registered molecules may be sub-sequentially turned off by bleaching, allowing adjacent molecules to be activated and become fluorescent. The sequence of registering molecules may be continued until the molecules are registered.

The techniques of sub diffraction resolution microscopy may include structured illumination microscopy (SIM) or multi-focal illumination microscopy (MSIM).

An advantage of sub diffraction resolution microscopy may be that all proteins may be potentially tagged with a fluorophoere, thus providing an image identifying all proteins within a cell. Sub diffraction resolution microscopy may be used to localize proteins, but cellular context may be limited in sub diffraction resolution microscopy images. Because cellular context may be limited in sub diffraction resolution microscopy, fiducial markers may be placed in a cell that may be used in registering the sub diffraction resolution microscopy image 405 with an image produced by the same and/or different modality.

Figure 5:
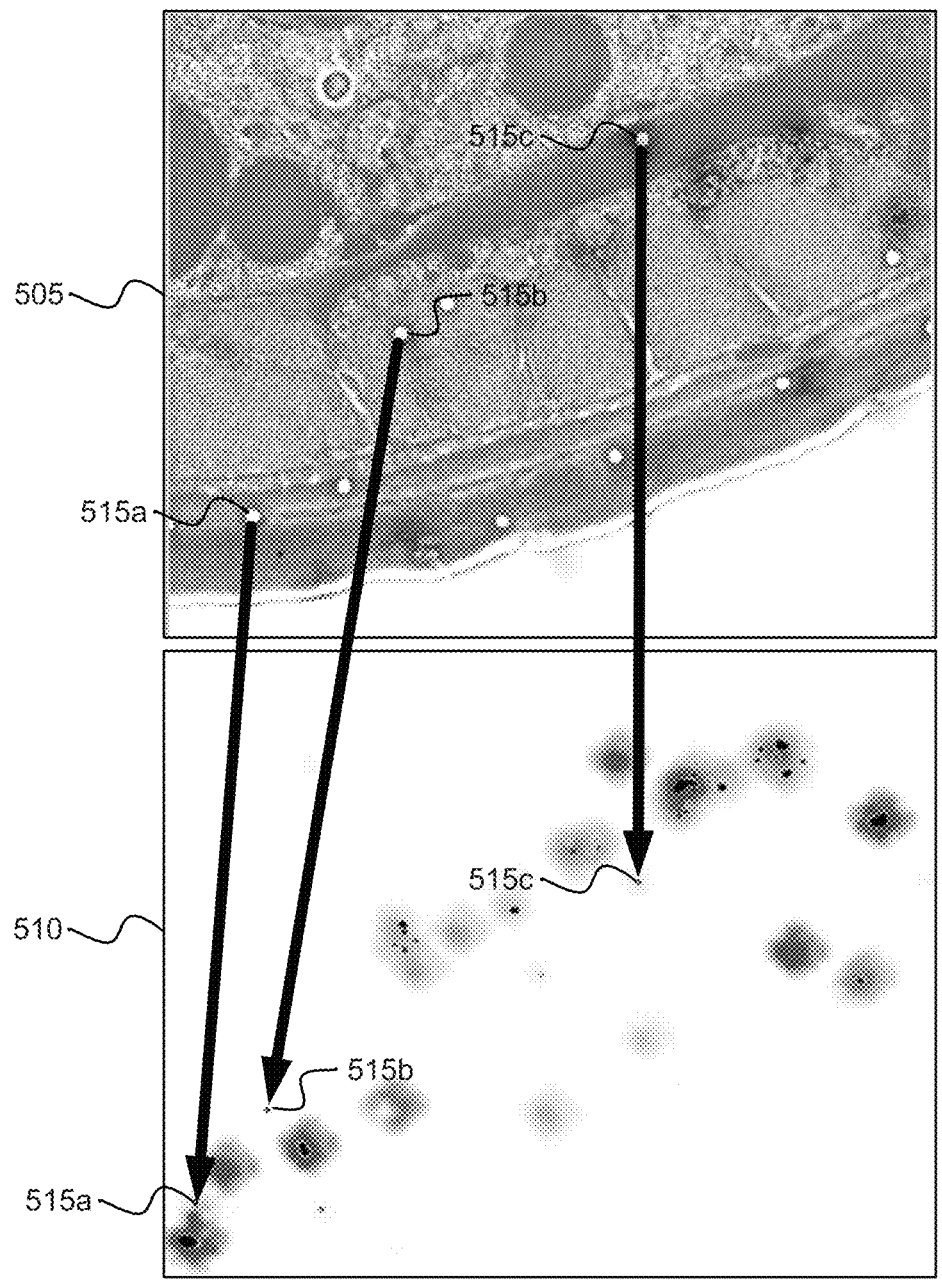
FIG. 5 is an illustration that depicts an example of the registration of feature markers in an electron microscopy image and a sub diffraction resolution microscopy image.

FIG. 5 is a visual example of a method that registers an electron microscopy image 505 with a sub diffraction resolution microscopy image 510. Previous methods for registering electron microscope and sub diffraction resolution modalities may involve manual alignment of two dimensional images with respect to each other using image manipulation software. Whereas the current technology may provide automation in registering two or more datasets representing microscopy images by executing a method on a computing device that registers the two or more datasets.

The microscopy images shown in FIG. 5 may be correlated by registering feature markers that may be common to both the electron microscopy image 505 and the sub diffraction resolution microscopy image 510. The feature markers in this example may be fiducial markers 515a-c, which may be introduced elements (e.g., gold nanoparticles, silver nanoparticles, silica beads, etc.) placed within the cell. The fiducial markers 515a-c may be visible in both images, and thus, represented in the datasets representing the images, and may be used in aligning the electron microscopy image 505 with the sub diffraction resolution microscopy image 510. For example, the fiducial marker 515a visible in the electron microscopy image 505 may be aligned with the fiducial marker 515a visible in the sub diffraction resolution microscopy image 510. The same alignment process may be performed for the fiducial marker 515b and 515c in the electron microscopy image 505 with the fiducial markers 515b and 515c in the sub diffraction resolution microscopy image 510.

An example method may illustrate this process where datasets may contain fiducial markers that may be imaged across acquisition modalities. The method may register the datasets by labeling the corresponding fiducial markers in both datasets and by solving a linear system to determine the affine transformation that appropriately maps the fiducial markers in the first modality to the same fiducial markers in the second modality. The process may include 1) finding the fiducial markers in each dataset and 2) finding the correspondence between the fiducial markers. Upon registering the fiducial markers, the data points of the datasets may be registered. In addition, the method may include the ability to skew a dataset so that any irregularities in an image that may have translated over into the dataset from the equipment used in the initial dataset capture may be corrected.

In a case where a dataset does not contain fiducial markers, similarity metrics may be used instead. The method may attempt to minimize joint entropy between the datasets using an iterative refinement process and register datasets based upon similarities between the datasets. For example, similarities in cell structures may be identified in the datasets and used as feature markers. Preprocessing filters may be applied to the datasets in an attempt to make the datasets similar in intensity and content, and therefore make similarities in the datasets more clear. In addition, smaller regions of interest may be determined and utilized in a dataset so that similarities in the smaller region may be more easily identified. If the datasets are not similar enough in nature for similarity metrics, or if the registration cannot be described with a rigid transformation due to sample warping, then non-linear transformation using thin-plate splines may be used to correlate the datasets.

In addition to two dimensional images, three dimensional images may be collected and registered using electron microscopy modalities and sub diffraction resolution modalities. A three dimensional electron microscopy data set may be captured via electron tomography, whereby a sample may be rotated with respect to the electron beam, creating a series of images that can be computationally reconstructed to form a volume. A three dimensional sub diffraction resolution microscope that extends the depth of imaging to the micron scale and beyond, while retaining the capability of detecting multiple targets simultaneously may be used to obtain a three dimensional sub diffraction resolution image. These three dimensional images may be used to generate datasets that may then be registered to form three dimensional volumetric visualizations of a specimen.

Figure 6:
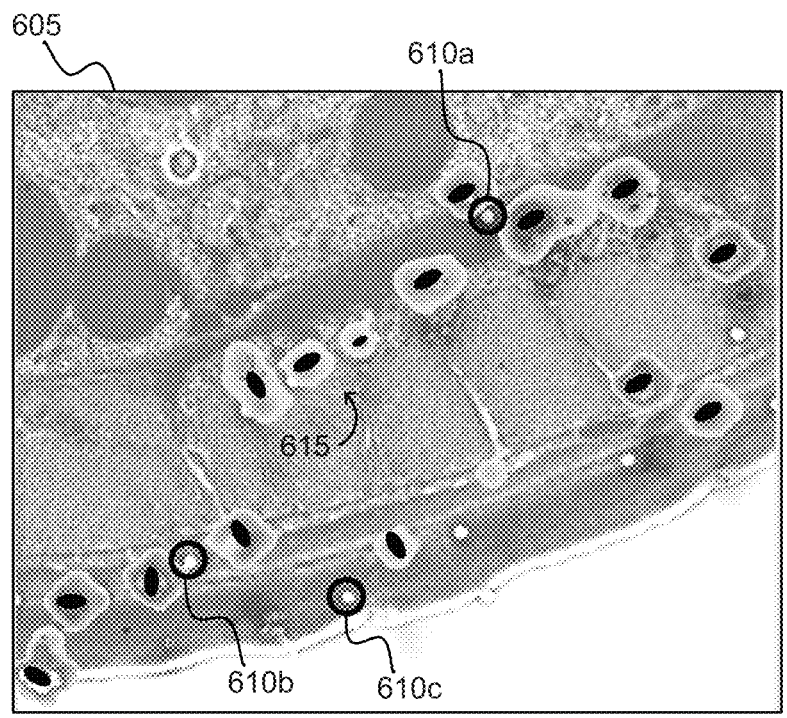
FIG. 6 is an illustration that depicts an example of a visualization of a combined dataset.

The results of the alignment of the fiducial markers 515a-c, and therefore the registration of the electron microscopy image 505 and the sub diffraction resolution microscopy image 510 are shown in FIG. 6. Upon correlating datasets by registering the feature markers of two or more datasets, a visualization may be provided from the combined dataset that may represent a combination of the datasets from the two or more modalities. FIG. 6 shows an image 605 of a cell with a depiction of subcellular structure and a number of proteins 615 within the subcellular structure. The subcellular structure of the cell may be an image obtained from an electron microscope and the proteins 615 within the subcellular structure may be an image obtained from a sub diffraction resolution microscope using fluorescence microscopy. The proteins in the image 605 may have been tagged with a fluorophore causing the protein to fluoresce when hit by a beam of light and therefore may be visible within the cell's subcellular structure in the image 605.

As described above, fiducial markers 610a-c may have been placed within the cell and may be present in the datasets used to create the image 605. In one example, the fiducial markers 610a-c may be removed from the dataset after the datasets have been registered. In another example, datasets and fiducial markers may be temporal. For instance, datasets may be created using live cell imaging, and those datasets may be added to dataset structures captured from other modalities based upon fiducial markers. The datasets may then be combined and formatted to display as video.

In addition to combining two or more datasets to form a combined dataset that may provide an image 605, a number of combined datasets may be joined along an edge of the of the combined datasets to form a mosaic. For example, images of different sections of a cell may be aligned to form a complete image of the cell, either at a two dimensional level or at a three dimensional level. In an example where images show the interaction of proteins with a cell's subcellular structure, the mosaic may provide a complete picture of protein localization within the cell. Providing researchers with a single visualization may enable researchers to map the distribution of proteins in a cell, which may lead to an understanding of the function of proteins in a cell.

Figure 7:
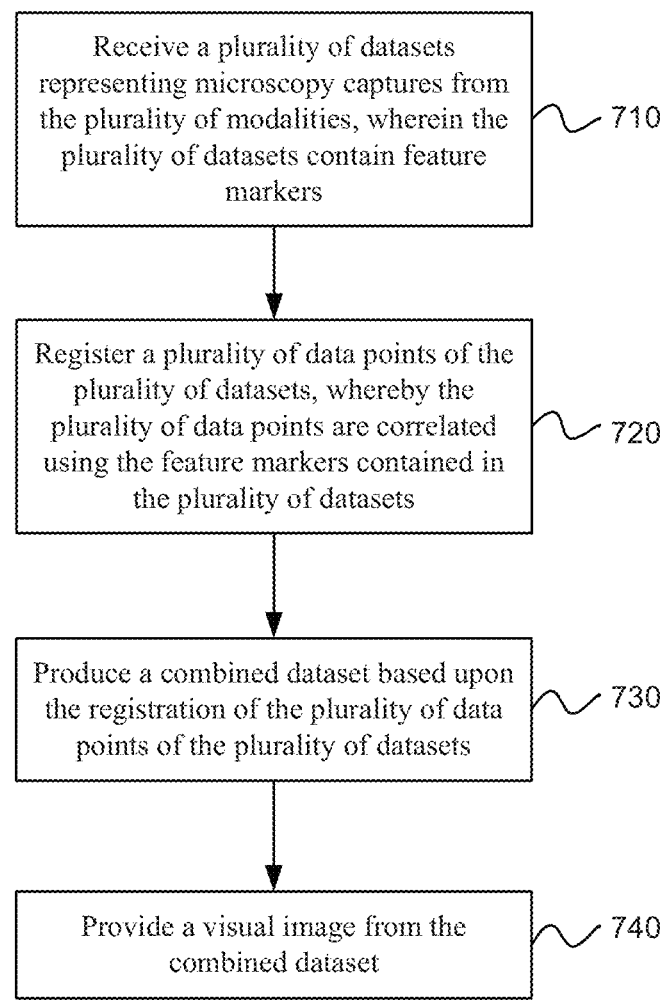
FIG. 7 is flowchart illustrating an example of a method to correlate microscopy images from a plurality of modalities in a sub diffraction resolution environment.

FIG. 7 is a flowchart illustrating an example method to correlate microscopy images from a number of modalities in a sub diffraction resolution environment. As in block 710, a number of datasets may be received that represent microscopy captures from a number of modalities. A modality may include an electron microscope and/or a sub diffraction resolution microscope. An electron microscope may produce a magnified image of a specimen by illuminating the specimen with an electron beam, whereas sub diffraction resolution microscopy may use fluorescence techniques capable of capturing images of a specimen at a nanometer-scale resolution. A microscopy capture may be an image of a specimen or a dataset representing an image of a specimen.

The specimen may contain a number of feature markers that may be captured using a modality and included in a dataset. For example, a feature marker may be a natural structure of a specimen, such as a landmark that may be a subcellular structure (e.g., organelle). Also, a feature marker may be an introduced landmark, such as a fiducial marker (e.g., gold nanoparticle, silver nanoparticle, silica bead, etc.). Introduced feature markers may be placed on a specimen prior to imaging the specimen with a modality, thus enabling the introduced feature marker to be visible in an image and/or dataset.

In addition to receiving datasets from different modalities, two or more datasets may be received from the same modality. The reason may be that if the field of view of the modality's microscope is too narrow to capture the desired specimen sample, multiple datasets may be stitched (i.e., joined at an edge) together to form one large dataset. There may be overlap between subsequent datasets, therefore the use of registration methods described in this specification may be used to align and combine the datasets.

In one example, a dataset that may contain irregularities as a result of preparing a specimen to be captured. These irregularities may be corrected using a modeling process prior to registering the dataset with one or more other datasets. For example, user-defined, non-linear image transformations may be used to account for specimen capture warping.

In an alternative example, feature markers contained in two or more captures may be recognized based upon a process that uses machine learning. For example, natural features that may be captured by a modality may be identified. A machine learning process may be trained to recognize the feature in a capture and the next time that the process encounters the feature, the process may identify the feature so that the feature may be used in registering two or more captures containing the same feature.

As in block 720, a number of data points contained in a dataset may be registered with data points of other datasets. In one example, registration may be accomplished by correlating the feature markers contained in the datasets. For example, feature markers may be identified in each dataset and a correspondence between the feature markers of the different datasets may be determined. Corresponding feature markers may then be labeled in the different datasets. Correlation of the data points may be accomplished by solving a linear system to determine the affine transformation that best maps the set of data points in one dataset to the same points in another dataset.

As in block 730, a combined dataset may be produced from a number of datasets based upon the registration of data points contained in the number of datasets. The combined dataset may represent an overlay of two or more images from a number of modalities. For example, the combined dataset may be an overlay of a sub diffraction resolution microscopy image on an electron microscopy image showing a distribution of proteins in the protein's cellular context.

Further, combined datasets may be combined with other combined datasets, whereby the combined datasets may be registered in the same way that captures from a number of modalities may be registered. Thus, like building blocks, combined datasets may be stacked and/or joined at the edges to form larger datasets in two or three dimensions that may provide a larger and/or more complete picture of a specimen.

The combined dataset than may be used to provide a visual image of the combined dataset, as in block 740. The combined dataset may create a model of the specimen captured by the different modalities. From the combined dataset model, a visualization may be produced that visually displays the combined modality captures. In one example, the combined dataset may be displayed as a three dimensional image using direct volume rendering, which allows the combined dataset to be represented as a semi-transparent cloud. In another example, the combined dataset may be rendered and displayed as a two dimensional image showing the combination of modality images.

While the flowcharts presented for this technology may imply a specific order of execution, the order of execution may differ from what is illustrated. For example, the order of two more blocks may be rearranged relative to the order shown. Further, two or more blocks shown in succession may be executed in parallel or with partial parallelization. In some configurations, one or more blocks shown in the flow chart may be omitted or skipped. Any number of counters, state variables, warning semaphores, or messages might be added to the logical flow for purposes of enhanced utility, accounting, performance, measurement, troubleshooting or for similar reasons.

Some of the functional units described in this specification have been labeled as modules, in order to more particularly emphasize their implementation independence. For example, a module may be implemented as a hardware circuit comprising custom VLSI circuits or gate arrays, off-the-shelf semiconductors such as logic chips, transistors, or other discrete components. A module may also be implemented in programmable hardware devices such as field programmable gate arrays, programmable array logic, programmable logic devices or the like.

Modules may also be implemented in software for execution by various types of processors. An identified module of executable code may, for instance, comprise one or more blocks of computer instructions, which may be organized as an object, procedure, or function. Nevertheless, the executables of an identified module need not be physically located together, but may comprise disparate instructions stored in different locations which comprise the module and achieve the stated purpose for the module when joined logically together.

Indeed, a module of executable code may be a single instruction, or many instructions and may even be distributed over several different code segments, among different programs and across several memory devices. Similarly, operational data may be identified and illustrated herein within modules and may be embodied in any suitable form and organized within any suitable type of data structure. The operational data may be collected as a single data set, or may be distributed over different locations including over different storage devices. The modules may be passive or active, including agents operable to perform desired functions.

The technology described here may also be stored on a computer readable storage medium that includes volatile and non-volatile, removable and non-removable media implemented with any technology for the storage of information such as computer readable instructions, data structures, program modules, or other data. Computer readable storage media include, but is not limited to, RAM, ROM, EEPROM, flash memory or other memory technology, CD-ROM, digital versatile disks (DVD) or other optical storage, magnetic cassettes, magnetic tapes, magnetic disk storage or other magnetic storage devices, or any other computer storage medium which may be used to store the desired information and described technology.

The devices described herein may also contain communication connections or networking apparatus and networking connections that allow the devices to communicate with other devices. Communication connections are an example of communication media. Communication media typically embodies computer readable instructions, data structures, program modules and other data in a modulated data signal such as a carrier wave or other transport mechanism and includes any information delivery media. A "modulated data signal" means a signal that has one or more of its characteristics set or changed in such a manner as to encode information in the signal. By way of example and not limitation, communication media includes wired media such as a wired network or direct-wired connection and wireless media such as acoustic, radio frequency, infrared and other wireless media. The term computer readable media as used herein includes communication media.

Reference was made to the examples illustrated in the drawings and specific language was used herein to describe the same. It will nevertheless be understood that no limitation of the scope of the technology is thereby intended. Alterations and further modifications of the features illustrated herein and additional applications of the examples as illustrated herein are to be considered within the scope of the description.

Furthermore, the described features, structures, or characteristics may be combined in any suitable manner in one or more examples. In the preceding description, numerous specific details were provided, such as examples of various configurations to provide a thorough understanding of examples of the described technology. It will be recognized, however, that the technology may be practiced without one or more of the specific details, or with other methods, components, devices, etc. In other instances, well-known structures or operations are not shown or described in detail to avoid obscuring aspects of the technology.

Although the subject matter has been described in language specific to structural features and/or operations, it is to be understood that the subject matter defined in the appended claims is not necessarily limited to the specific features and operations described above. Rather, the specific features and acts described above are disclosed as example forms of implementing the claims. Numerous modifications and alternative arrangements may be devised without departing from the spirit and scope of the described technology.

Reference was made to the examples illustrated in the drawings and specific language was used herein to describe the same. It will nevertheless be understood that no limitation of the scope of the technology is thereby intended. Alterations and further modifications of the features illustrated herein and additional applications of the examples as illustrated herein are to be considered within the scope of the description.

Furthermore, the described features, structures, or characteristics may be combined in any suitable manner in one or more examples. In the preceding description, numerous specific details were provided, such as examples of various configurations to provide a thorough understanding of examples of the described technology. One skilled in the relevant art will recognize, however, that the technology may be practiced without one or more of the specific details, or with other methods, components, devices, etc. In other instances, well-known structures or operations are not shown or described in detail to avoid obscuring aspects of the technology.

Although the subject matter has been described in language specific to structural features and/or operations, it is to be understood that the subject matter defined in the appended claims is not necessarily limited to the specific features and operations described above. Rather, the specific features and acts described above are disclosed as example forms of implementing the claims. Numerous modifications and alternative arrangements may be devised without departing from the spirit and scope of the described technology.

What is claimed is:

1. A method to correlate a fluorescence microscopy image with an electron microscopy image in a sub diffraction resolution environment, comprising:
   under control of a processor and memory configured with executable instructions, receiving a first dataset representing a fluorescence microscopy capture containing a plurality of feature markers;

receiving an electron microscopy capture containing a plurality of feature markers;

registering a plurality of data points of the first dataset with the electron microscopy image to align the plurality of feature markers of the first dataset with the plurality of feature markers of the electron microscopy capture; and forming a combined visualization based upon the registering of the plurality of data points of the first dataset and the electron microscopy capture.

2. The method as in claim 1, further comprising repeating steps of receiving a first dataset, receiving an electron microscopy image, registering and joining the combined visualization with one or more combined visualizations.

3. The method as in claim 1, wherein forming a combined visualization further comprises providing a two dimensional visualization.

4. The method as in claim 1, wherein forming a combined visualization further comprises providing a three dimensional visualization.

* * * * *